United States Patent
Joshi et al.

(10) Patent No.: US 12,263,032 B2
(45) Date of Patent: Apr. 1, 2025

(54) HEMODYNAMIC PARAMETER ESTIMATION

(71) Applicant: KONINKLIJKE PHILIPS N.V., Eindhoven (NL)

(72) Inventors: Rohan Joshi, Eindhoven (NL); Ralph Wilhelm Christianus Gemma Rosa Wijshoff, Munstergeleen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 153 days.

(21) Appl. No.: 18/009,077

(22) PCT Filed: Jun. 11, 2021

(86) PCT No.: PCT/EP2021/065731
§ 371 (c)(1),
(2) Date: Dec. 8, 2022

(87) PCT Pub. No.: WO2021/250224
PCT Pub. Date: Dec. 16, 2021

(65) Prior Publication Data
US 2023/0210492 A1      Jul. 6, 2023

(30) Foreign Application Priority Data

Jun. 11, 2020   (EP) .................................. 20179433

(51) Int. Cl.
*A61B 8/06*   (2006.01)
*A61B 8/00*   (2006.01)
*A61B 8/08*   (2006.01)

(52) U.S. Cl.
CPC ............ *A61B 8/065* (2013.01); *A61B 8/4416* (2013.01); *A61B 8/488* (2013.01)

(58) Field of Classification Search
CPC ....... A61B 8/065; A61B 8/4416; A61B 8/488; A61B 8/06; A61B 8/5223; A61B 5/02007;
(Continued)

(56) References Cited

U.S. PATENT DOCUMENTS 6,319,205 B1    11/2001  Goor
11,969,236 B2 *  4/2024  Wang .................. A61B 5/0022
(Continued)

OTHER PUBLICATIONS

Liu Songsong et al: "A compensation method for blood pressure estimation by pulse transit time", 2013 IEEE International Conf. of IEEE Region 10, Oct. 22, 2013, pp. 1-3.
(Continued)

*Primary Examiner* — Alexei Bykhovski

(57) ABSTRACT

An apparatus and method for estimating one or more hemodynamic parameters such as cardiac output or stroke volume. Embodiments are based on the concept of incorporating information about vascular tone into hemodynamic parameter estimation to improve accuracy. More particularly, embodiments use a measurement of a time duration for a blood pulse to travel from the heart along a certain length of an arterial path as a proxy measure for vascular tone, and incorporate this into hemodynamic parameter estimation. Embodiments are also based on incorporating vascular tone proxy measurements for multiple different arterial paths to take account of vascular tone variations between different portions of the circulatory system.

15 Claims, 3 Drawing Sheets

(58) Field of Classification Search
CPC ............ A61B 5/02028; A61B 5/02125; A61B 5/02416; A61B 5/0295; A61B 5/352; A61B 5/7267; A61B 5/029
See application file for complete search history.

(56) References Cited

U.S. PATENT DOCUMENTS

| | | | |
|---|---|---|---|
| 2008/0033305 A1* | 2/2008 | Hatib | A61B 5/0285 |
| | | | 600/485 |
| 2009/0187110 A1 | 7/2009 | Voss | |
| 2015/0324962 A1 | 11/2015 | Itu | |
| 2015/0366514 A1 | 12/2015 | Fantini | |
| 2016/0095522 A1* | 4/2016 | Wiard | A61B 5/0265 |
| | | | 600/483 |
| 2017/0251929 A1* | 9/2017 | Barodka | A61B 5/6828 |
| 2018/0078155 A1* | 3/2018 | Baek | G16H 50/30 |
| 2022/0117553 A1* | 4/2022 | Chahine | A61B 5/0535 |

OTHER PUBLICATIONS

International Search Report Dated Sep. 8, 2021 for International Appln No. PCT/EP2021/065731 Filed Jun. 11, 2021.

* cited by examiner

HEMODYNAMIC PARAMETER ESTIMATION

CROSS-REFERENCE TO PRIOR APPLICATIONS

This application is the U.S. National Phase application under 35 U.S.C. § 371 of International Application No. PCT/EP2021/065731, filed on Jun. 11, 2021, which claims the benefit of European Application No. 20179433.6 filed on Jun. 11, 2020. These applications are hereby incorporated by reference herein.

FIELD OF THE INVENTION

This invention relates to an apparatus and method for estimating one or more hemodynamic parameters.

BACKGROUND OF THE INVENTION

For assessing hemodynamic stability, various hemodynamic parameters are important to measure and monitor. These include for example central hemodynamic parameters such as cardiac output (CO), stroke volume (SV), and their variation over time.

Cardiac output (CO) is defined as the amount of blood pumped from the heart per minute [Liters/min] and is hence affected by two factors, the heart rate (HR) [beats/min] and the stroke volume (SV), where the stroke volume is the volume of blood pumped from the left ventricle of the heart into the aorta with each beat [L/beat].

Central hemodynamic parameters such as these can be measured invasively or non-invasively. Typically, this may involve obtaining measures of blood flow in one or more arteries. Blood flow, Q, is defined as the volume of blood flowing through a vessel per unit time. It can be expressed mathematically as $Q=vA$, where Q is blood flow at a location along an arterial path, v is blood velocity at said location (cm/s), and A (ml/s) is the cross-sectional area of the vessel at said location ($cm^2$).

Various non-invasive measurement methods exist, including for example use of ultrasound sensing means to measure blood flow through major arteries, for example using Doppler ultrasound. Other methods of measuring blood flow are also known such as using blood pressure measurements to indirectly determine blood flow.

As schematically illustrated in FIG. 1, in known methods, blood flow is typically measured in one of the branches 14a-14n of the vascular tree (in one artery), and this blood flow measurement can then be used to estimate one or more hemodynamic parameters. This can be done for example by using a pre-determined algorithm or transfer function which takes the blood flow measurement as an input and provides a hemodynamic parameter estimation as an output. FIG. 1 schematically illustrates blood flow from the heart 12 through the various arterial branches 14a-14n of the circulatory system. The volumetric blood output from the heart in each heart beat is the stroke volume (SV), and the volumetric output per minute is the cardiac output (CO).

Such methods are simple and fast, but are known to lack accuracy. By only acquiring a blood flow measurement in a single branch of the arterial system, hemodynamic parameter estimations may be inaccurate as flow rate may vary in different arterial branches. Furthermore, known estimation methods are not able to take into account differences in autoregulation and vasoconstriction properties which exist for different arterial branches.

Improved methods for obtaining non-invasive estimates of hemodynamic parameters would therefore generally be of value in this field.

SUMMARY OF THE INVENTION

The invention is defined by the claims.

According to examples in accordance with an aspect of the invention, there is provided a controller, adapted to determine an estimate of at least one hemodynamic parameter of a subject, the controller adapted to:

receive an input indicative of an arterial flow measurement in at least one arterial path of the subject, the arterial path being a central arterial path or a peripheral arterial path, obtain for each of a central arterial path and a peripheral arterial path a measure indicative of a time difference, ΔT, between a heart blood ejection event and arrival of a corresponding pulse wave at a pre-determined location along the respective arterial path, as a result of blood flow from the heart to the location, determine an estimate of the hemodynamic parameter based on a combination of: the blood flow measurement from the at least one arterial path, and the time difference measure, ΔT, for each of the central and peripheral arterial paths.

Embodiments of the invention are based on the insight that known approaches to estimating hemodynamic parameters, such as cardiac output or stroke volume, can be improved by taking account of vascular tone in different branches of the arterial system. Vascular tone refers to the degree of constriction experienced by a blood vessel at any given time relative to its maximally dilated state. All arterial and venous blood vessels (under normal conditions) exhibit a degree of smooth muscle contraction that determines the diameter, and hence tone, of the vessel. Vascular tone in any given local area may vary at any given time depending upon the hemodynamic conditions, and is regulated by competing vasoconstrictor and vasodilator influences. The function of vascular tone variations is twofold: to regulate arterial blood pressure globally in the body, and also to regulate local blood flow within an organ. The vascular tone in an arterial path at any given time thus has an effect on measurable hemodynamic parameters such as cardiac output and stroke volume. Furthermore, since vascular tone varies in different arterial paths, an accurate estimation of the hemodynamic parameters should take account of this variation.

Vascular tone is difficult to measure directly. Embodiments of the present invention are based on the realization that the time taken for blood to travel from the heart along a pre-determined length of an arterial path is dependent upon the vascular tone of the arterial path. The two are correlated with one another. In view of this, it is the realization of the inventors that this time duration can be used as a proxy measure for vascular tone in a given arterial path.

There are two standard clinical measurements which give an indication of this time duration: pulse arrival time (PAT) and pulse transit time (PTT), and certain embodiments of the invention make use of these clinical measurements to provide the ΔT measurement. However, use of these standard measurements is not essential for deriving the ΔT measurement.

Thus, in summary, embodiments of the invention are based on integrating information about the vascular tone of different arterial paths in the circulatory system into the determination of central hemodynamic parameters to improve their accuracy. Proxy measures of the vascular tone are estimated by calculating the time taken for blood to travel along a length of one or more arterial paths (e.g. pulse arrival time (PAT) or pulse transit time (PTT)). This can then be integrated into an algorithm or calculation or transfer function, in combination with an arterial blood flow measurement for at least one arterial path (preferably the central arterial path), to determine one or more hemodynamic parameters.

This allows the calculation to be sensitive to differential autoregulation in different arterial paths, including dynamic changes in vascular tone. This results in more accurate estimates of central hemodynamic parameters. Accurate estimates of central hemodynamic parameters allow for improved clinical decisions and medical interventions, and thus improved medical outcomes for patients.

The blood flow measurement is a measurement of volumetric blood flow per unit time at a measurement location in the arterial path. In other words, the blood flow measurement is a measurement of volume of blood flowing through an arterial path (e.g. flowing past a measurement location in the arterial path) per unit time. It can be expressed mathematically as $Q=vA$, where Q is blood flow (ml/s) at a location along an arterial path, v is blood velocity at said location (cm/s), and A is the cross-sectional area of the vessel at said location ($cm^2$).

The controller may be adapted to provide the blood flow measurement for the at least one arterial path, and the measures indicative of the time difference, $\Delta T$, for both the central and peripheral arterial path, or parameters derived therefrom, as inputs to a pre-determined transfer function, wherein the transfer function is adapted to generate the estimate for the at least one hemodynamic parameter based on the inputs.

In other words the controller is adapted to process the blood flow measurement for the at least one arterial path, and the time difference measure, $\Delta T$, or parameters derived therefrom, for both the central and peripheral arterial path, with the transfer function to generate the estimate for the at least one hemodynamic parameter.

The transfer function may define or embody a pre-determined functional relationship between the inputs and the at least one hemodynamic parameter. The transfer function may generate the hemodynamic parameter based on this pre-determined functional relationship and based on the inputs.

The transfer function may in some examples be a classical algorithmic function, and/or may be a machine learning model. It may comprise a linear function of the inputs. In some examples, it may be a multiparametric linear regression model which models the target hemodynamic parameter as a linear sum of each of the input parameters, each input parameter weighted by a respective weighting coefficient.

The controller is preferably further adapted to generate a data output indicative of the estimate of the at least one hemodynamic parameter. This may be a data packet comprising data representative of the estimate, or a series of values thereof derived over a period of time, ready for data export, for example to a datastore or a user interface, or along a network communication channel. The method may comprise transmitting the data output to a further module or device, e.g. to a user interface.

In advantageous embodiments, ultrasound monitoring technology can be used to detect the blood flow and/or $\Delta T$ parameters. For example, Doppler ultrasound can be used to acquire the blood flow measurement.

To determine the at least one hemodynamic parameter, the inputs of the at least one blood flow measurement and the $\Delta T$ measurements can be combined using a pre-determined function, equation, or algorithm. Machine learning engines can also be used to derive the hemodynamic parameter from the inputs. These various approaches will be referred to generally herein as a transfer function.

For example a pre-determined or pre-stored function (transfer function) can be used which embodies a pre-determined functional relationship between the inputs and which can compute the at least one hemodynamic parameter based on the inputs. The transfer function may simply be a mathematical relationship between several input parameters and a central hemodynamic parameter which serves as the output.

To derive such a transfer function, machine learning and/or statistical methods can for example be applied to a labeled dataset. For example, multi-parametric regression has been used successfully in trials to estimate such a transfer function using a clinical dataset. Given sufficient data, the transfer function can also be improved using patient metadata, e.g. gender, BMI, and other patient personal information.

An arterial path means for example a longitudinal section of a certain length along one or more arteries of the circulatory system.

A peripheral arterial path means an arterial path in the peripheral vascular system, i.e. the part of the circulatory system that consists of the arteries not in the head, chest or abdomen (e.g. in the arms, hands, legs and feet).

A central arterial path means a path in the central vascular system, i.e. arteries in the head, chest, abdomen or neck for example.

Preferably the blood flow measurement may be derived from at least a central arterial path, e.g. the carotid artery. However, it may also be derived from a different arterial path including a peripheral arterial path. Blood flow measurements may be derived from both a peripheral and central arterial path in some examples. The at least one arterial path from which the blood flow measurement is derived is preferably one of the same two arterial paths (central and peripheral) from which $\Delta T$ measurements are derived.

A heart ejection event means an event corresponding to the ejection of blood from the heart, i.e. a heart beat event, i.e. systolic phase of the heart. The event can be a defined reference point during the process of the blood ejection, e.g. during the systolic phase of the heart cycle, e.g. a point at the end of the pre-ejection period, when the aorta opens and blood is beginning to be ejected from the left ventricle. In other examples, the event may be a point at the beginning of the pre-ejection period, when the heart is first electrically activated and begins to contract.

The obtaining of the measure, $\Delta T$, indicative of the time difference may comprise receiving at the controller an input indicative of the time difference for each of the two arterial paths. In other examples, it may comprise a processing or calculation step. For example, the controller may be adapted to receive for each arterial path a signal input indicative of a detection of arrival of the pulse wave at the pre-determined location along the arterial path, and an input indicative of detection of the ejection event, and to determine the time duration, $\Delta T$, for each arterial path.

Although two arterial paths are mentioned in descriptions above and examples herein, in further embodiments, a $\Delta T$ time difference may be determined for more than two arterial paths. A blood flow measurement may be obtained for more than one arterial path, or even more than two arterial paths.

The controller may then be adapted to determine the at least one hemodynamic parameter based on a combination of the $\Delta T$ values and the blood flow measurement(s) for all of the arterial paths.

Determining the hemodynamic parameter may be based on use of a pre-determined transfer function or algorithm. A transfer function means a function which takes at least one blood flow measurement and $\Delta T$ measurements for the two or more arterial paths as an input and computes an estimate of at least one hemodynamic parameter as an output. The transfer function may simply be a mathematical relationship between several input parameters and a central hemodynamic parameter which serves as the output. This has been discussed above and will be discussed further below.

The transfer function may comprise a machine learning algorithm. Various implementation options in this regard will be outlined in greater detail below.

The transfer function may for example be stored locally on a memory, the memory being comprised by the controller or the controller being operatively coupled to the memory. The transfer function may be embodied in programming of the controller itself in some examples.

According to one set of examples, the obtaining of the time difference measure for each arterial path may comprise obtaining a pulse arrival time (PAT) measurement for each arterial path.

The ejection event in this case may correspond to the point of electrical activation of the heart. It corresponds to the point at the beginning of the pre-ejection period, where the heart pulse first begins.

By way of example, this can be detected as the time of occurrence of the QRS complex in an ECG signal. It may correspond to the time of occurrence of a particular reference point within the QRS complex, such as one of the Q, R, and S peaks (e.g. the R-peak, which is the largest peak). It may correspond to the time of occurrence of the start of the QRS complex.

However, use of ECG to detect this event is not essential and other means such as use of an accelerometer or inductive sensing means or radar sensing means can alternatively be used.

In some approaches, PAT can be measured using ECG (electrocardiography) and PPG (photoplethysmography) sensor measurements. ECG can be used to detect the onset of the QRS complex as the start of the electrical activation of the heart and PPG can be used to detect the start of the pulse wave at the downstream location along the arterial path via optical measurements of the blood volume. Both measurements are standard measurements in clinical practice.

According to one or more embodiments, the obtaining of the time difference measure, $\Delta T$, for each arterial path may comprise obtaining a pulse transit time (PTT) measurement for each arterial path. The pulse transit time is the time between ejection of the blood into the aorta and the arrival of the corresponding pulse-wave at the downstream measurement location. In other words it is the time between the end of the pre-ejection period (PEP) and the arrival of the pulse wave at the pre-determined location along the arterial path.

In some embodiments, the obtaining of the PTT measurement for each arterial path may comprise: obtaining a PAT measurement for each arterial path, obtaining an estimate of a pre-ejection period (PEP) duration, and determining the PTT measurement for each arterial path by subtracting the PEP duration from the PAT measurement for each arterial path.

Pre-ejection period (PEP) is a term of the art, and is the time period measured from the electrical activation of the heart (indicated for instance by the QRS complex in an ECG signal) until the ejection of the blood from the heart in the aortic artery. It is the time between the electrical activation of the heart and the opening of the aortic valve.

The pulse arrival time (PAT) is thus related to the PEP by: PAT=PEP+PTT, where PTT is the pulse transit time.

There are different ways of obtaining an estimate of the PEP.

According to one set of examples, the estimate of the PEP duration may be derived based on use of an input from a phonocardiography (PCG) sensing means and/or an impedance cardiography (ICG) measurement means. For example, the opening of the aortic valve and the ejection of the blood each generate a distinctive high-pitch sound: a snap sound for the opening, and a click sound for the ejection. One or both of these can be identified in a PCG reading, occurring after the first heart sound. This can be used to detect the time occurrence of the ejection event for example.

Furthermore, an ICG and ECG can additionally or alternatively be used together to directly identify PEP. A method for doing this is outlined in detail in the paper: René van Lien, Nienke M Schutte, Jan H Meijer and Eco J C de Geus, Estimated preejection period (PEP) based on the detection of the R-wave and dZ/dt-min peaks in ECG and ICG, 18 Apr. 2013, IOP Publishing Ltd.

Measurements from these sensing modalities can be used to identify the time instant at which the aortic valve opens. From this can be determined the time between the electrical activation of the heart (e.g. beginning or other reference point of the QRS complex of an ECG measurement) and the opening of the aortic valve (at which point the pressure wave begins travelling along the arterial system). This period corresponds to the pre-ejection period.

In other examples, the controller may use a pre-determined estimate for the pre-ejection period, i.e. a reference value, which may for instance be stored in a local memory or retrieved from a remote data source such as a remote server.

In accordance with one or more embodiments, the hemodynamic parameter may be determined based on variation in the time difference values, $\Delta T$, over time for each arterial path. For this set of embodiments, the controller may be configured to obtain a plurality of time difference measurements, $\Delta T$, for each of the arterial paths, corresponding to different heart cycles, and determine a measure indicative of variation in the $\Delta T$ values over time for each arterial path, and determine the estimate of the hemodynamic parameter based on the variation in $\Delta T$ values.

According to one or more embodiments, the determining of the estimate of the hemodynamic parameter comprises determining a quotient between the $\Delta T$ value(s) for the peripheral path and central path. In other words, the estimate of the hemodynamic parameter may be based on a quotient $\Delta T\_cen/\Delta T\_peri$, where $\Delta T\_cen$ is the time difference, $\Delta T$, value for the central arterial path, and $\Delta T\_peri$ is the time difference, $\Delta T$, value for the peripheral arterial path. The quotient may be calculated in the inverse manner in other examples, i.e. $\Delta T\_peri/\Delta T\_cen$.

Detecting changes or variation in the vascular tone proxy measures ($\Delta T$ values) and/or their ratios (in case of multiple proxy measures) indicates changes in the (relative) tone of the measured branches of the vascular tree. These changes can indicate both localized and more systemic changes in the vascular tone of the arterial system. By incorporating these measurements into the calculation of the hemodynamic parameters, more accurate estimates are obtained.

The at least one hemodynamic parameter calculated by the controller may include at least one of: cardiac output, stroke volume, and stroke volume variation (SVV). Other examples of hemodynamic parameters which could be derived include: blood velocity, stroke volume variation, systolic velocity, diastolic velocity, blood pressure.

The details of the transfer function may vary depending upon the hemodynamic parameter to be derived. The transfer function may embody a mathematical relationship between the input parameters and the output hemodynamic parameter(s). Hence for different target hemodynamic parameters, this relationship may differ, e.g. the weights applied to the different inputs in the calculation, as well as potentially the inputs used to calculate it (where there are for example additional inputs, further to the blood flow and ΔT measurements).

The controller may be configured to obtain the at least one measure indicative of the blood flow measurement using an ultrasound sensing means. The ultrasound sensing means may comprise one or more ultrasound transducers. It may comprise an ultrasound transducer unit or probe for example, configured to generate ultrasound pulse emissions and to detect reflected ultrasound echo signals.

The ultrasound sensing means may output ultrasound data to the controller or may output calculated blood flow measurements directly to the controller. The ultrasound sensing means may acquire Doppler ultrasound data. The ultrasound sensing means may in some examples further comprise a dedicated ultrasound processing unit for extracting from the acquired ultrasound data one or more blood flow measurements, and to supply these to the controller for estimating the hemodynamic parameter.

By way of an advantageous example, wearable ultrasound sensors can be used to monitor blood flow in arteries, e.g. placed over the at least one arterial path, for example, the carotid artery. This can measure the blood flowing through the arterial path.

It is noted that the use of ultrasound in the context of the present invention is particularly advantageous since ultrasound sensing has a versatility to acquire a range of different information, and is entirely non-invasive. Furthermore, these ultrasound-based features can be combined in several ways according to one or more embodiments, to provide meaningful information such as the blood flow waveform which is a product of the cross-sectional area and the velocity waveform.

For example, in the context of embodiments of the present invention, ultrasound-based measurements may be acquired using Pulse Wave Doppler ultrasound measurements, which can be used to yield a (blood flow) velocity waveform. From this waveform, useful features such as the peak systolic velocity, maximum velocity and many others can be extracted.

It is also possible to derive relevant information from B-mode ultrasound data or measurements. This can be used for example to derive a waveform for the blood vessel diameter.

However, use of ultrasound is not essential. An alternative for example to use of ultrasound is to obtain blood flow measurements indirectly using blood pressure measurements. This will be explained in greater detail to follow.

According to one or more embodiments, the controller may be configured, for at least one of the arterial paths, to obtain both a measure of arterial flow and a measure of a time of arrival of the pulse wave at the pre-determined location along the arterial path, using the same single ultrasound sensing means. Thus, the same component can be used for the dual function of detecting pulse arrival and measuring blood flow. This therefore limits the total number of components.

The controller may be configured, for at least one of the arterial paths, to detect the time of arrival of the pulse wave at the pre-determined location along the arterial path using a PPG sensor. For example, the peripheral arterial path may be the arterial path which runs along the arm of the subject, and a PPG sensor for attachment to a finger of the subject may be used to detect arrival of a pulse wave at the finger of the subject. This represents just one example, mentioned for reasons of illustration only and is not intended to limit the invention.

According to some examples, the ejection event mentioned above may be a moment of electrical activation of the heart, corresponding to the start of the pre-ejection period.

In some alternative examples, the ejection event may correspond to a point at the end of the pre-ejection period.

The controller may be configured to detect the occurrence of the ejection event using an ECG sensor input.

For example, where the ejection event is a point corresponding to the start of the pre-ejection period, detecting the occurrence of the ejection event may comprise detecting the time at the beginning of the QRS complex in the ECG signal.

Use of ECG is just one example means. Alternative means for detecting occurrence of ejection events include use of inductive sensors, radar sensors, accelerometers, or heart rate sensors such as chest heart rate sensor bands.

Examples in accordance with one or more embodiments may further provide an apparatus for deriving an estimate of at least one hemodynamic parameter, comprising
- a first sensor means for detecting a heart ejection event;
- a second sensor means for coupling to a location along an arterial path of a subject, for detecting time of arrival of a blood pulse wave from the heart at said location;
- a third sensor means for detecting blood flow through the arterial path; and
- a controller in accordance with any example or embodiment outlined above or described below, or in accordance with any claim of this application, operatively coupled with the first, second and third sensor means.

The first, second and third sensor means may correspond to different respective sensor devices, or one or more of the sensor means may correspond to the same sensor device.

The first sensor means may be an ECG sensor arrangement in some examples.

The second sensor means may comprise a PPG sensor for optically coupling to said location.

The third sensor means may be an ultrasound sensing means.

Thus, at least one set of embodiments may include an apparatus for deriving an estimate of at least one hemodynamic parameter, comprising:
- an ECG sensor arrangement for detecting a heart ejection event;
- at least one PPG sensor for optically coupling to a location along an arterial path of a subject, for detecting time of arrival of a blood pulse wave from the heart at said location;
- an ultrasound sensing means for detecting blood flow through at least one arterial path; and
- a controller in accordance with any example or embodiment outlined above or described below, or in accordance with any claim of this application, operatively coupled with the ECG sensor arrangement, at least one PPG sensor and the ultrasound sensing means.

Alternative example sensor means to these also exist, as discussed above, and discussed further below.

The ultrasound sensing means may comprise an ultrasound transducer arrangement. It may be configured to detect blood flow using Doppler ultrasound measurements. It may include a dedicated ultrasound processing unit for extracting from the acquired ultrasound data one or more blood flow measurements, and to supply these to the controller for use in estimating the hemodynamic parameter.

Examples in accordance with a further aspect of the invention provide a computer-implemented method for determining an estimate of at least one hemodynamic parameter, the method comprising:

receiving an input indicative of an arterial flow measurement of at least one arterial path of the subject, the arterial path being a central or a peripheral arterial path;

obtaining for each of a central arterial path and a peripheral arterial path a measure indicative of a time difference, $\Delta T$, between a heart ejection event and arrival of a corresponding pulse wave at a pre-determined location along the respective arterial path, as a result of blood flow from the heart to the location; and determining an estimate of the hemodynamic parameter based on a combination of: the blood flow measurement of the at least one arterial path, and the time difference measure, $\Delta T$, for each arterial path.

The determining may for example comprise providing the blood flow measurement for the at least one arterial path, and the measures indicative of the time difference, $\Delta T$, for both the central and peripheral arterial path, or parameters derived therefrom, as inputs to a pre-determined transfer function, and wherein the transfer function is adapted to generate the estimate for the at least one hemodynamic parameter based on the inputs and a pre-determined functional relationship between the inputs and the at least one hemodynamic parameter.

The method preferably further comprises generating a data output indicative of the estimate of the at least one hemodynamic parameter.

The invention also provides a computer program product comprising a computer readable medium, the computer readable medium having computer readable code embodied therein, the computer readable code being configured such that, on execution by a suitable computer or processor, the computer or processor is caused to perform a method in accordance with any example or embodiment outlined above or described below, or in accordance with any claim of this application.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
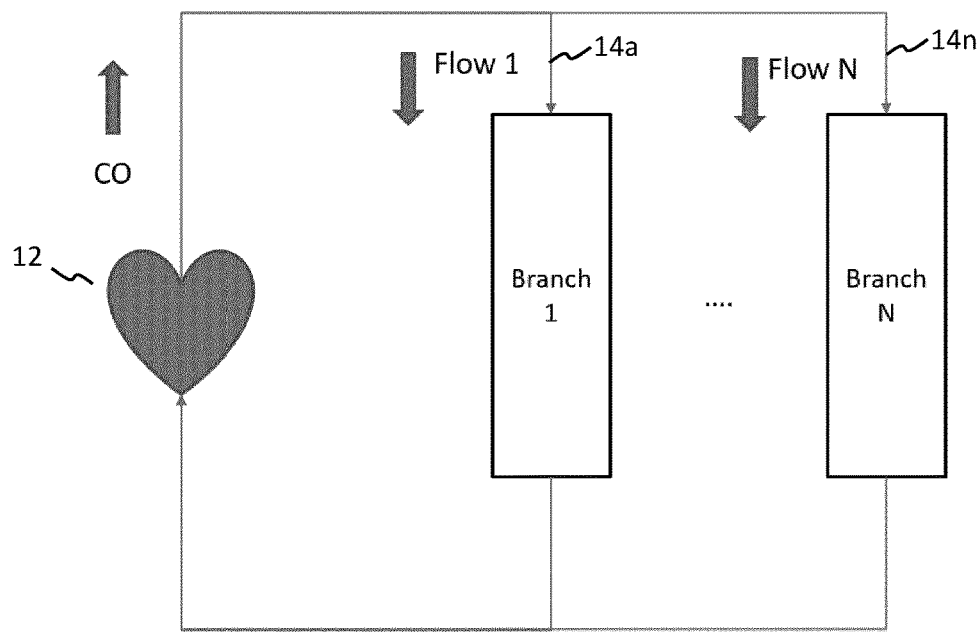
FIG. 1 schematically illustrates blood flow through different branches of an arterial system.

The invention will be described with reference to the FIGS.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the FIGS. are merely schematic and are not drawn to scale. It should also be understood that the same reference numerals are used throughout the FIGS. to indicate the same or similar parts.

The invention provides an apparatus and method for non-invasively estimating one or more hemodynamic parameters such as cardiac output or stroke volume. Embodiments are based on incorporating information about vascular tone into hemodynamic parameter estimation to improve accuracy. More particularly, embodiments use a measurement of a time duration, $\Delta T$, of the travel of a blood pulse wave from the heart along a certain length of an arterial path as a proxy measure for vascular tone, and incorporate this into hemodynamic parameter estimation. Embodiments are also based on incorporating vascular tone proxy measurements for multiple different arterial paths to take account of vascular tone variations between different portions of the circulatory system.

Known methods for estimating hemodynamic parameters are typically based on acquiring a measurement for arterial flow in a single artery, for example the neck, and deriving an estimate of a central hemodynamic parameter (such as cardiac output or stroke volume) using a transfer function which incorporates an algorithm or computation equation able to compute a hemodynamic parameter estimate from the flow measurement input.

However, such estimation methods typically assume that the arterial flow in a single location is representative of the total arterial flow in the whole vascular tree. However, this assumption is not accurate. As a result, currently known methods for estimating hemodynamic parameters are unable to take account of differential autoregulation conditions in different portions of the circulatory system. For example, variations in vascular tone occur due to both to systemic global factors affecting the whole of the circulatory system (such as regulation of blood pressure), and also due to local factors such as local regulation of blood flow in particular organs. Thus, a more accurate hemodynamic parameter estimation should preferably take account of possible variations in factors such as vascular tone in different sections of the circulatory system. For example, differences can be expected to exist in these factors between the central portion of the circulatory system and peripheral portions of the circulatory system.

To illustrate this, a case may be considered in which a blood flow measure at the carotid artery (central arterial system) is acquired and used to estimate the total cardiac output (CO). The body regulates the blood flow through the carotid artery to supply sufficient oxygen and nutrients to the brain. However, at the same time, a blood flow to a peripheral region e.g. the arm, may be increased or decreased due to a certain event, e.g. due to movement or straining of the arm. This causes the total CO to increase or decrease accordingly. However, this is not detectable in any change in blood flow through the carotid artery, since the flow through the carotid artery is regulated according to the needs of the brain. Thus, it is not possible to obtain an accurate estimate of the total CO from only the central (carotid) arterial flow measurement.

However, by taking into account also peripheral measurements (such as peripheral PAT or PTT), variations in blood output to peripheral regions can be detected and combined with the central arterial flow measurements to improve the estimate of the total CO. It is this principle upon which embodiments of the present invention are based.

According to examples in accordance with an aspect of the invention, there is provided a controller, adapted to derive an estimate of at least one hemodynamic parameter of a subject, the controller adapted to:

- receive an input indicative of an arterial flow measurement in at least one arterial path of the subject, the arterial path being a central arterial path or a peripheral arterial path;
- obtain for each of a central arterial path and a peripheral arterial path a measure indicative of a time difference, $\Delta T$, between a heart blood ejection event and arrival of a corresponding pulse wave at a pre-determined location along the respective arterial path, as a result of blood flow from the heart to the location; and
- determine an estimate of the hemodynamic parameter based on a combination of: the blood flow measurement of the at least one arterial path, and the time difference measure, $\Delta T$, for each arterial path.

Embodiments are aimed at remedying the inaccurate assumption that the flow through one branch of the vascular tree is representative of the flow through all other branches. Embodiments are based on obtaining longitudinal proxy measures of the vascular tone of at least two branches of the vascular tree. By incorporating these measurements in the hemodynamic parameter calculation, it is possible to arrive at more accurate estimates.

Vascular tone is difficult to measure directly. Embodiments of the present invention are based on the realization that the time taken for blood to travel from the heart along a pre-determined length of an arterial path (in other words, how fast cardiac pulses travel through branches of the vascular tree) is closely dependent upon vascular tone of the arterial path. The two are correlated with one another. In view of this, this time duration can be used as a proxy measure for vascular tone in the arterial path.

Thus, in summary, embodiments of the invention are based on integrating information about the vascular tone of different arterial paths in the circulatory system into the determination of central hemodynamic parameters to improve their accuracy. This information is combined with blood flow information and fed as an input to a transfer function which produces as an output an estimate of a hemodynamic parameter such as cardiac output.

Figure 2:
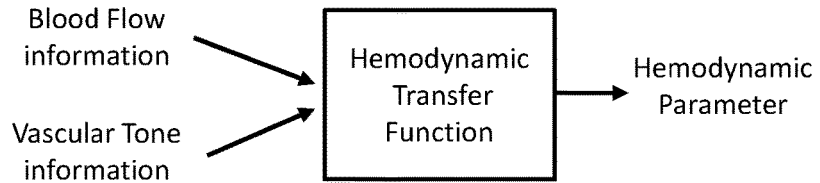
FIG. 2 schematically illustrates the general concept of the present invention.

This general principle is depicted schematically in FIG. 2. Embodiments of the present invention are based on providing information related to, or indirectly indicative of, vascular tone, in combination with information related to blood flow, to for example a hemodynamic transfer function. The transfer function is configured to generate as an output an estimate of one or more hemodynamic parameters based on the input information.

According to one or more embodiments, proxy measures of the vascular tone can be estimated by calculating the time taken for blood to travel along a length of one or more arterial paths (e.g. pulse arrival time (PAT) or pulse transit time (PTT)). This can then be integrated into an algorithm or calculation (transfer function), in combination with at least arterial blood flow measurement (preferably for at least the central arterial path, but optionally alternatively for a peripheral path), to determine one or more hemodynamic parameters.

This allows the calculation to be sensitive to differential autoregulation in different arterial paths, including dynamic changes in vascular tone. This results in more accurate estimates of central hemodynamic parameters. Accurate estimates of central hemodynamic parameters allow for improved clinical decisions and medical interventions, and thus improved medical outcomes for patients.

An arterial path means for example a longitudinal section of a certain length along one or more arteries of the circulatory system.

A peripheral arterial path means an arterial path in the peripheral vascular system, i.e. the part of the circulatory system that consists of the arteries not in the head, chest or abdomen (e.g. in the arms, hands, legs and feet).

A central arterial path means a path in the central vascular system, i.e. arteries in the head, chest, abdomen or neck for example.

A heart ejection event means an event corresponding to the ejection of blood from the heart, i.e. a heart beat event, i.e. systolic phase of the heart. The event can be a defined reference point during the process of the blood ejection, e.g. a point at the end of the pre-ejection period, when the aorta opens and blood is beginning to be ejected from the left ventricle. In other examples, the event may be a point at the beginning of the pre-ejection period, when the heart is first electrically activated and begins to contract.

Although two arterial paths are mentioned in descriptions above and examples herein, in further embodiments, a $\Delta T$ time difference may be determined for more than two arterial paths. A blood flow measurement may be obtained for more than one arterial path, or even more than two arterial paths. The controller may then be adapted to determine the at least one hemodynamic parameter based on a combination of the $\Delta T$ values and the blood flow measurement(s) for all of the arterial paths.

Figure 3:
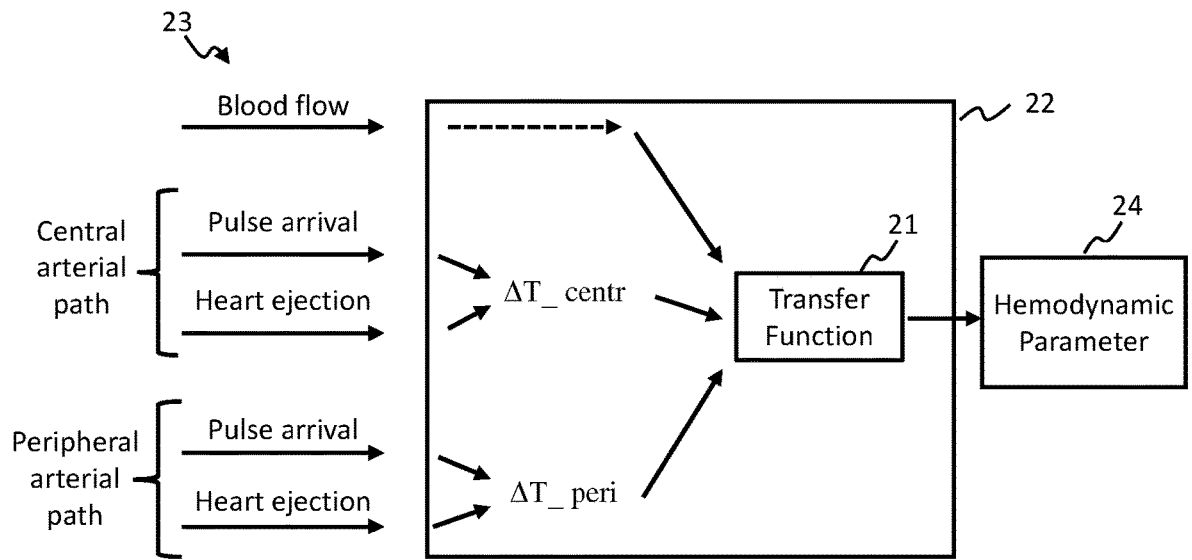
FIG. 3 schematically illustrates the processing workflow of an example controller according to one or more embodiments.

The general principal of the present invention is schematically outlined in FIG. 3 which schematically depicts an example controller 22 which receives a set of inputs 23, performs a computation process using the inputs, and generates at least one output corresponding to an estimate of at least one hemodynamic parameter 24. In particular, the controller 22 receives a set of inputs for the central arterial path, a set of inputs for the peripheral arterial path, and also at least one blood flow measurement input, corresponding to blood flow through at least one of the central and peripheral arterial paths. Preferably, it is a measurement of the central arterial path. In further examples, blood flow measurements for both the central and peripheral arterial paths may be received as inputs. Furthermore, inputs for both the central and two or more peripheral arterial paths may be received in further embodiments. Furthermore, inputs for two or more central arterial paths may be received in some embodiments.

The inputs for the central arterial path include, an input indicative of time of arrival of a pulse wave at the predetermined location along the central arterial path, and an input indicative of a time of occurrence of heart ejection event. Using the time of arrival of the pulse wave and the time of the heart ejection event, a time difference, $\Delta T\_centr$, between these two events can be calculated.

A similar set of inputs is also received for the peripheral arterial path. Using the time of arrival of the pulse wave and the time of the heart injection event, a time difference, $\Delta T\_peri$, between these two events can be calculated for the peripheral arterial path.

Although FIG. 3 shows the controller 22 receiving separate inputs for each of the central and peripheral arterial paths corresponding to the heart ejection event, a single input may be received to the controller indicative of occurrence of the heart ejection event.

The at least one blood flow measurement (e.g. for the central arterial path), and the time difference values, $\Delta T\_centr$ and $\Delta T\_peri$, are then utilized by the controller 22 in deriving a hemodynamic parameter 24. By way of example, the hemodynamic parameter may, by way of non-limiting example, be cardiac output (CO) of the subject, stroke volume (SV) of the subject, stoke volume variation (SVV) of the subject, or stroke volume index (SVI) of the subject.

Determining the estimate of the hemodynamic parameter 24 may be based on application of a pre-defined algorithm or computation function by the controller. For example, a pre-determined transfer function 21 may be applied by the controller 22 which is configured to receive as an input the at least one flow measurement, and the time difference values, $\Delta T$, of the two or more arterial paths and to generate an output indicative of one or more hemodynamic parameter estimates based on the inputs. By way of illustration, the transfer function 21 is shown schematically in FIG. 3. As discussed above, the $\Delta T$ values provide proxy measures of vascular tone in each of the two arterial paths, which enable the algorithm or computation or transfer function applied by the controller 22 to derive more accurate hemodynamic parameter estimation 24.

For example a pre-determined or pre-stored function (transfer function) 21 can be used which embodies a pre-determined functional relationship between the inputs and which can compute the at least one hemodynamic parameter based on the inputs. The transfer function may simply be a mathematical relationship between several input parameters and a central hemodynamic parameter which serves as the output. It may comprise a machine learning algorithm or engine which has been trained using labelled data to derive a particular hemodynamic parameter based on input blood flow and $\Delta T$ measurements.

To derive a transfer function, machine learning and/or statistical methods can for example be applied to a labeled dataset. For example, multi-parametric regression has been used successfully in trials to estimate such a transfer function based on a clinical dataset. Given sufficient data, the transfer function can also be improved using patient metadata, e.g. gender, BMI, and other patient personal information. Other approaches to providing a transfer function may include for instance use of support vector machines or Naïve Bayes models.

By way of example, the transfer function may according to one or more embodiments include any type of machine learning algorithm, such as a logistic regression model, decision tree algorithm, artificial neural network, support vector machine or Naïve Bayesian model, or any other type of machine learning algorithm, may be provided which is then trained using a training dataset comprising prior acquired data for one or more patients.

Methods of training a machine-learning algorithm are well known. Typically, such methods comprise obtaining a training dataset, comprising training input data entries and corresponding training output data entries. The training input data entries in this case would be the acquired inputs for the transfer function, i.e. at least the measured $\Delta T$, PAT, PTT or $\Delta PAT$ values for each of the two arterial paths, and the at least one blood flow measurement. Additional inputs could also be included in some embodiments. The training output data entries would correspond to the hemodynamic parameter being sought, e.g. cardiac output, stroke volume, and/or stroke volume variation, et cetera. To build up the training data, the hemodynamic parameter would be measured manually, e.g. using an invasive method, when acquiring the training data entries, so that its accuracy is assured.

An initialized machine-learning algorithm is applied to each input data entry to generate predicted output data entries. An error between the predicted output data entries and corresponding training output data entries is used to modify the machine-learning algorithm. This process can be repeated until the error converges, and the predicted output data entries are sufficiently similar (e.g. ±1%) to the training output data entries. This is commonly known as a supervised learning technique.

The resulting trained algorithm could then, according to one or more embodiments, provide the required transfer function.

There are different ways of obtaining the set of inputs for the two or more arterial paths. In particular, there are different ways of obtaining the arterial flow measurement for the at least one arterial path of the subject, and of obtaining the measure indicative of a time difference, $\Delta T$, between the heart blood ejection event and arrival of a corresponding pulse wave at a pre-determined location along each of the two respective arterial paths. For example, different sensor modalities can be used to derive these measurement inputs.

Various possible means or approaches to obtaining these measurement inputs will now be briefly outlined in general terms. A set of more detailed embodiments will then be outlined subsequently.

According to one set of examples, the obtaining of the time difference measure for each arterial path may comprise obtaining a pulse arrival time (PAT) measurement for each arterial path.

The ejection event in this case may correspond to the point of electrical activation of the heart. It corresponds to the point at the beginning of the pre-ejection period, where the heart pulse first begins.

The ejection event may be detected using an ECG sensor. By way of example, this can be detected as the time of occurrence of the start of the QRS complex in an ECG signal. However, use of ECG to detect this event is not essential and other means can alternatively be used. Alternative means include use of inductive sensors, radar sensors, accelerometers, or heart rate sensors such as chest heart rate sensor bands.

The time of arrival of the pulse wave at the pre-determined location along the arterial path may be detected using a PPG sensor in some examples. Alternatively, an ultrasound sensing means may be used to detect the arrival of the pulse wave, e.g. an ultrasound transducer unit configured to acquire Doppler ultrasound data at the pre-determined pulse arrival location.

According to one or more embodiments, the obtaining of the time difference measure, ΔT, for each arterial path may comprise obtaining a pulse transit time (PTT) measurement for each arterial path. The pulse transit time is the time between ejection of the blood into the aorta and the arrival of the corresponding pulse-wave at the downstream measurement location. In other words it is the time between the end of the pre-ejection period (PEP) and the arrival of the pulse wave at the pre-determined location along the arterial path.

In some embodiments, the obtaining of the PTT measurement for each arterial path may comprise: obtaining a PAT measurement for each arterial path, obtaining an estimate of a pre-ejection period (PEP) duration, and determining the PTT measurement for each arterial path by subtracting the PEP duration from the PAT measurement for each arterial path.

Pre-ejection period (PEP) is a term of the art, and is the time period measured from the electrical activation of the heart (indicated for instance by the QRS complex in an ECG signal) until the ejection of the blood from the heart in the aortic artery. It is the time between the electrical activation of the heart and the opening of the aortic valve.

The pulse arrival time (PAT) is thus related to the PEP by: PAT=PEP+PTT, where PTT is the pulse transit time.

There are different ways of obtaining an estimate of the PEP.

According to one set of examples, the estimate of the PEP duration may be derived based on use of an input from a phonocardiography (PCG) sensing means and/or an impedance cardiography (ICG) measurement means.

Measurements from these sensing modalities can be used to identify the time instant at which the aortic valve opens. From this can be determined the time between the electrical activation of the heart (e.g. beginning of the QRS complex of an ECG measurement) and the opening of the aortic valve (at which point the pressure wave begins travelling along the arterial system). This period corresponds to the pre-ejection period.

For example, the opening of the aortic valve and the ejection of the blood each generate a distinctive high-pitch sound: a snap sound for the opening, and a click sound for the ejection. One or both of these can be identified in a PCG reading, occurring after the first heart sound. This can be used to detect the time occurrence of the ejection event.

Furthermore, an ICG and ECG can additionally or alternatively be used together to directly identify PEP. A method for doing this is outlined in detail in the paper: Rend van Lien, Nienke M Schutte, Jan H Meijer and Eco J C de Geus, Estimated preejection period (PEP) based on the detection of the R-wave and dZ/dt-min peaks in ECG and ICG, 18 Apr. 2013, IOP Publishing Ltd.

In other examples, the controller may use a pre-determined estimate for the PEP, which may for instance be stored in a local memory or retrieved from a remote data source such as a remote server.

The controller may be configured to obtain the measure indicative of the blood flow measurement for at least one of the arterial paths using an ultrasound sensing means. The ultrasound sensing means may comprise one or more ultrasound transducers. It may comprise an ultrasound transducer unit or probe for example.

The ultrasound sensing means may output ultrasound data to the controller or may output calculated blood flow measurements directly to the controller. The ultrasound sensing means may acquire Doppler ultrasound data. The ultrasound sensing means may in some examples further comprise a dedicated ultrasound processing unit for extracting from the acquired ultrasound data one or more flow measurements, and to supply these to the controller for estimating the hemodynamic parameter.

Use of ultrasound sensing is just one example means for detecting blood flow. One further alternative is to obtain blood flow measurements indirectly using blood pressure measurements for example.

For example, it is possible to derive an estimate of cardiac output from a non-invasive blood pressure measurement. First, a non-invasive continuous arterial blood pressure waveform is obtained from a finger by applying a cuff around the middle phalanx and applying the well-known volume-clamping method. Using a model, the brachial arterial blood pressure waveform can be derived from the measured finger arterial blood pressure waveform. Finally, by applying the pulse contour analysis method to the brachial arterial pressure waveform it is possible to obtain an estimate of cardiac output. This can be used to give an estimate of blood flow.

The pulse contour method referred to above uses for example the area under a systolic portion of the blood pressure curve, in combination with for example a Windkessel model, and optionally also certain patient data such as age, gender, height and weight to come to an estimate of the stroke volume. This provides an indication of the cardiac output when combined with the heart rate. From this, blood flow information can be derived. This is for instance described in the paper: Truijen et al., Noninvasive continuous hemodynamic monitoring, J Clin Monit Comput (2012) 26:267-278.

There will now be outlined a series of particular embodiments of the invention to further illustrate and exemplify the principles of the inventive concept.

Figure 4:
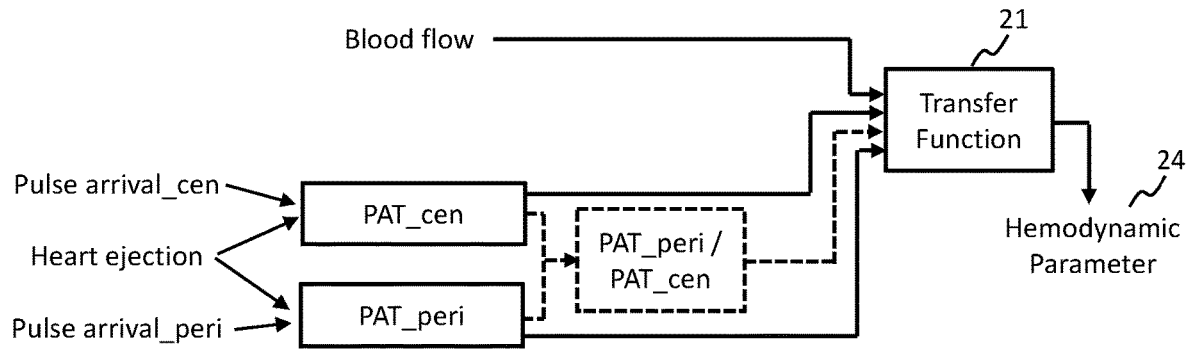
FIG. 4 schematically illustrates processing workflow according to a further example embodiment.

FIG. 4 schematically outlines the processing workflow for a first example set of embodiments.

According to this set of embodiments, pulse arrival time (PAT) is used as the proxy measure for vascular tone. In other words, the measure of the time difference ΔT, between the heart ejection event and the pulse arrival is obtained by acquiring a PAT measurement for each of the peripheral and central arterial path.

For example, the peripheral arterial path may be an arterial path extending from the heart along the arm to the finger. The central arterial path may be a path extending from the heart toward the head, via passage along the neck.

In operation, a PPG sensor may be positioned at a stable location along the peripheral arterial path. For example a finger-clip PPG sensor may be used and coupled to a finger of the subject. This PPG sensor may be used to detect the time of arrival of each pulse wave from the heart at the finger following each ejection event ("Pulse arrival_peri"). This may correspond for example to a peak or other characteristic reference point in the PPG sensor output. Example reference points for detection in the raw PPG pulse waveform include, for instance, the time of the systolic minimum, the time instant of the diastolic maximum, the time of maximum systolic slope, or any other characteristic point.

Alternatively, the pulse arrival at the peripheral arterial path distal location may be measured by other sensing modalities, such as an ultrasound (US) sensor, accelerometer (ACC), or a ballistocardiogram measurement for instance.

An ECG sensing apparatus may be used to detect the time of the ejection event in the heart ("Heart ejection"). For example, a set of at least two ECG electrodes may be positioned on the chest of the subject for sensing electrical activity of the heart. These may be attached to a dedicated ECG sensing processor arranged to detect the electrical signals using the electrodes. Each time the heart contracts (systolic phase) to eject blood from the left ventricle for pumping through the arterial tree, a characteristic electrical signal is detectable in the ECG output. This signal pattern is known as the QRS complex, and consists of a characteristic pattern of three peaks, Q-peak, R-peak, S-peak. Thus, the ejection event can be detected by detection of the QRS complex in the ECG signal, for example the start of the QRS complex, or the time of a particular peak in the QRS complex such as the R-peak (typically the largest peak).

In some examples, an ultrasound sensing means may further be used, and arranged for example to perform ultrasound sensing at the neck of the subject, for example at a location along the central arterial path (e.g. over the carotid artery). This ultrasound sensing means may comprise one or more ultrasound transducers, and a dedicated ultrasound processing unit for processing the acquired ultrasound data. The ultrasound data may be Doppler ultrasound data. The time of arrival of the pulse wave at the defined location along the central arterial path ("pulse arrival_cen") may be detected using the ultrasound sensing means. For example, Doppler ultrasound data provides an indication of blood flow through the arterial path, and thus arrival of a pulse wave at the given location can be detected by a sudden increase in flow, or the beginning of an upward slope in flow rate.

The same ultrasound sensing means can also be used to derive a measure of the arterial flow through the central arterial path, for example by acquiring and processing Doppler ultrasound data.

Alternatively, a measure of blood flow may be obtained using a different sensing modality, as discussed in more detail above. A measure of blood flow is needed from at least one arterial path and this is preferably the central arterial path but can alternatively be the peripheral arterial path. Optionally, blood flow measurements from both the central and peripheral arterial paths can be acquired and used in deriving the hemodynamic parameter estimate.

Note that in alternative examples, a further PPG sensor can be used instead of the ultrasound sensor to detect the pulse arrival at the location along the central arterial path, e.g. placed on the nose, forehead or ear concha.

Using these acquired measurements, a measure of the pulse arrival time (PAT) is derived for the central and peripheral arterial paths. The PAT is defined as the time difference between the time instant of the QRS complex in the electrocardiography (ECG) signal and the time of arrival of the corresponding pulse in a distal location. Thus, a PAT for the central arterial path ("PAT_cen") can be derived by calculating a difference between the time of the heart ejection event and the time of the pulse arrival at the distal point along the central arterial path (Pulse arrival_cen). Likewise, a PAT for the peripheral arterial path ("PAT_peri") can be derived by calculating a difference between the time of the heart ejection event and the time of the pulse arrival at the distal point along the peripheral arterial path ("Pulse arrival_peri").

In some examples, PAT_cen, PAT_peri, and the blood flow measurement for the at least one arterial path are then fed by the controller to the processing algorithm or computation or transfer function 21 and used to derive the estimate of the hemodynamic parameter 24 (e.g. cardiac output or stroke volume).

According to further examples, optionally, a quotient or ratio may be calculated between the PAT_cen and PAT_peri measurements, and this quotient then further used in calculating the estimated hemodynamic parameter 24. This value may be used in place of the individual PAT_cen and PAT_peri values, or in addition to these values, in calculating the estimated hemodynamic parameter.

Variations in the measurement of PAT_cen indicate changes in the vascular tone of the central branch and variations in the measurement of PAT_peri indicate changes in the vascular tone of the peripheral branch. Furthermore, the ratio PAT_peri/PAT_cen indicates differential changes of vascular tone. It is noted that the quotient may alternatively be calculated in the inverse form PAT_cen/PAT_peri.

It is noted that in acquiring the various measurement inputs discussed above (PPG, ECG, ultrasound), it is assumed that all of the measurement or sensor devices are synchronized in time, with an accuracy in the order of milliseconds, so that the time difference calculations are sufficiently accurate.

In various examples, different combinations of measurements or parameters may be used as the inputs for calculating the final estimated hemodynamic parameter. These include for example a combination of two or more PAT measurements for different respective central arterial paths; a combination of two or more PAT measurements for different respective peripheral arterial paths; a combination of at least one PAT measurement for a central arterial path and at least one PAT measurement for a peripheral arterial path; a single quotient of PAT_cen and PAT_peri, or multiple quotients for multiple different pairs of central and peripheral arterial paths.

Although in the example discussed above, an ECG sensing apparatus is used to identify the ejection event (the start of the heart contraction), other measurement or detection means are also possible. A non-limiting set of further possible means for detecting the ejection event include: one or more accelerometers, e.g. on the sternum (ballistocardiogram); one or more inductive sensors placed near to the heart; a radar sensor placed near to the heart, a transesophageal ultrasound probe; or a chest heart rate sensor, such as a chest band heart rate sensor.

Figure 5:
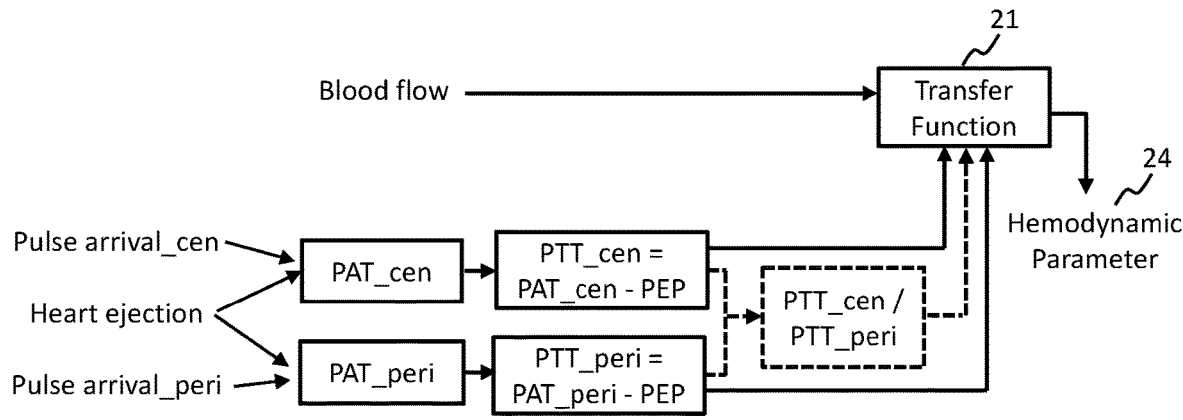
FIG. 5 schematically illustrates processing workflow according to a further example embodiment.

FIG. 5 schematically outlines the processing workflow for a second example set of embodiments.

This set of embodiments differs from that of FIG. 4 only in that a pulse transit time (PTT) measurement is used as the proxy measure for vascular tone instead of pulse arrival time (PAT). In other words, the measure of the time difference ΔT, between the heart ejection event and the pulse arrival is obtained by acquiring a PTT measurement for each of the peripheral and central arterial path. In all other respects, the features and workflow of this set of embodiments may be the same as described above for the example of FIG. 4. Thus, for brevity, the common features will not be described again in detail here.

To obtain the PTT measurement for each arterial path, it is necessary to correct the PAT value for the pre-ejection period (PEP), which is the time during which the heart is building up pressure, until the point at which it exceeds the aortic pressure and the aortic valve opens. Excluding the PEP leads to a more accurate proxy measure of vascular tone because during this period no pulse is traveling through the arterial paths.

The obtaining of the PTT measurement for each arterial path may thus comprise: obtaining a PAT measurement for each arterial path, obtaining an estimate of a pre-ejection period (PEP) duration, and determining the PTT measurement for each arterial path by subtracting the PEP duration from the PAT measurement for each arterial path. This is outlined in FIG. 5 which shows how a respective PTT value is obtained for each of the central arterial path (PTT_cen) and the peripheral arterial path (PTT_peri) by subtracting the PEP period from the respective PAT values for the two arterial paths.

There are different ways of obtaining the estimate of the PEP duration.

In some examples, the PEP duration may be derived based on use of an input from a phonocardiography (PCG) sensing means and/or an impedance cardiography (ICG) measurement means.

Measurements from these sensing modalities can be used to identify the time instant at which the aortic valve opens. From this can be determined the time between the electrical activation of the heart (beginning of the QRS complex of an ECG measurement) and the opening of the aortic valve (at which point the pressure wave begins travelling along the arterial system). This period corresponds to the pre-ejection period (PEP).

As discussed above, the opening of the aortic valve generates a distinctive high-pitch sound: a snap sound for the opening, and a click sound for the ejection. One or both of these can be identified in a PCG reading, occurring after the first heart sound. This can be used to detect the time occurrence of the aortic valve opening, which can then be used to determine the PEP.

In other examples, the controller 22 may use a pre-determined estimate for the pre-ejection period, which may for instance be stored in a local memory or retrieved from a remote data source such as a remote server.

In some examples, PTT_cen, PTT_peri, and the blood flow measurement for the at least one arterial path are then fed by the controller to the processing algorithm or computation or transfer function 21 and used to derive the estimate of the hemodynamic parameter 24 (e.g. cardiac output or stroke volume).

According to further examples, optionally, a quotient or ratio may be calculated between the PTT_cen and PTT_peri measurements, and this quotient then further used in calculating the estimated hemodynamic parameter. This value may be used in place of the individual PTT_cen and PTT_peri values, or in addition to these values, in calculating the estimated hemodynamic parameter 24.

Again, it is noted that in acquiring the various measurement inputs discussed above (PPG, ECG, ultrasound), it is assumed that all of the measurement or sensor devices are synchronized in time, with an accuracy in the order of milliseconds, so that the time difference calculations are sufficiently accurate.

Figure 6:
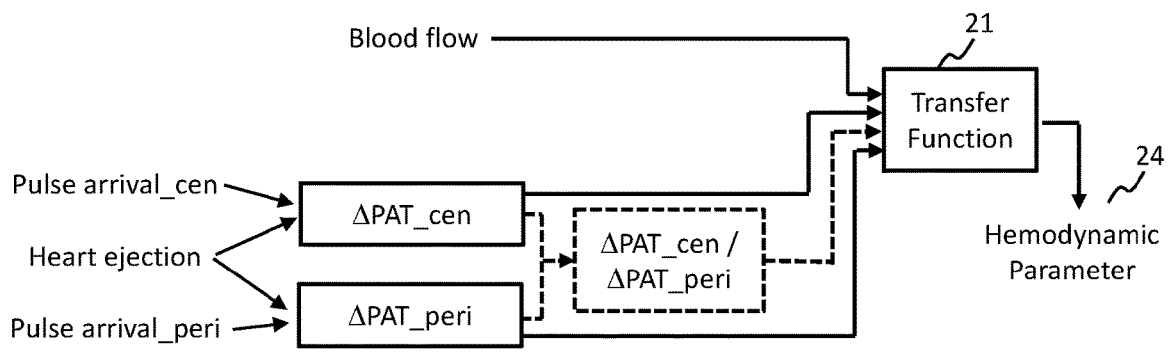
FIG. 6 schematically illustrates processing workflow according to a further example embodiment.

FIG. 6 schematically outlines the processing workflow for a third set of embodiments.

In this set of embodiments, the controller is configured to detect changes or variations in the vascular tone proxy measures for each arterial path over time. This provides an indication of changes in the (relative) tone of the measured branches of the vascular tree. These changes can indicate both localized and more systemic changes in the vascular tree which can further enhance the accuracy of the hemodynamic parameter estimation at any given time.

By way of example, the controller may be configured to obtain a plurality of time difference measurements, $\Delta T$, for each of the arterial paths, corresponding to different heart cycles, and determine a measure indicative of variation in the $\Delta T$ values over time for each arterial path, and determine the estimate of the hemodynamic parameter 24 based on the variation in $\Delta T$ values. The controller may continuously or recurrently re-acquire a $\Delta T$ value for each arterial path to thereby monitor the variations in the $\Delta T$ values as a function of time.

By way of example, and as illustrated in FIG. 6, the controller may be configured to monitor variations or changes in PAT values for each of the central and peripheral arterial paths. For example, for each new heart beat, the controller may obtain a new PAT measurement for each of the arterial paths, and calculate a difference, $\Delta$PAT, between the new PAT value and the preceding PAT value for the respective arterial path. These PAT change values for the central ($\Delta$PAT_cen) and peripheral ($\Delta$PAT_peri) arterial paths are then fed by the controller to a transfer function 21 to calculate the hemodynamic parameter in combination with the blood flow measurement information.

In other words, the controller uses values of the increase or decrease in PAT between heart beats as the parameter for calculating the hemodynamic parameter, not the absolute PAT values.

Optionally, a quotient or ratio may be calculated between the $\Delta$PAT_cen and $\Delta$PAT_peri measurements, and this quotient then further used in calculating the estimated hemodynamic parameter. This value may be used in place of the individual $\Delta$PAT_cen and $\Delta$PAT_peri values, or in addition to these values, in calculating the estimated hemodynamic parameter.

Although changes in PAT values is used in the example outlined above, the same principle can be applied for changes in PTT values for example.

The means for obtaining each of the measurement inputs for calculating the PAT values and for obtaining the blood flow measurement(s) may be the same as set out above for the example embodiments of FIG. 4 and FIG. 5 and thus will not be outlined again here in detail.

In contrast with the embodiments of FIGS. 4 and 5 discussed above, for this set of embodiments according to FIG. 6, in acquiring the various measurement inputs discussed above (PPG, ECG, ultrasound), it is not necessary that all of the measurement devices are synchronized in time. For example, where more than one measurement device is being used to acquire inputs (e.g. ultrasound, PPG, ECG etc.), it may be possible that they are not perfectly time-synchronized. A way to resolve this is to artificially force or impose synchronization by aligning common fiducial points of acquired time series of data from two or more measurement devices.

This process can be achieved for example by first identifying in the signals from each measurement device pre-defined fiducial points (characteristic anchor points). The points may be physiological in nature, or induced by the user, e.g. due to motion or through electromagnetic means. In each case, the points correspond to events which are known to leave a signal or trace on the signals from each of the measurement devices.

Once these common fiducial points have been identified in each signal, the signals can be time-aligned according to these points, i.e. so that corresponding fiducial points in each of the signals are in alignment in the time domain.

Above have been discussed a number of embodiments which make use of a transfer function or algorithm to determine an estimate of a hemodynamic parameter based on two or more input parameters. Various options for implementing the transfer function have been briefly outlined above.

One particular example approach is to use a parametric regression model to map a set of input parameters to a set of output parameters. The principles of application of such an example transfer function will now be outlined in more detail, for purposes of further explanation and illustration. The same principles may be applied in accordance with any of the above described embodiments for combining the particular sets of inputs outlined in each embodiment to thereby derive the estimated hemodynamic parameter.

This following example transfer function uses multiparametric regression modeling employing three input parameters. By way of example, the cardiac output (CO) is estimated using a transfer function having the following input parameters (independent variables):
  arterial blood flow ("Flow") at the carotid (e.g., based on pulse wave Doppler ultrasound measurement), and
  the measure indicative of the time difference between a heart ejection event and arrival of a corresponding pulse wave at a pre-determined location along the respective arterial path at each of a central arterial path ($\Delta T_{centr}$) and a peripheral arterial path ($\Delta T_{peri}$).

The transfer function can be estimated based on the following formula:

$$CO = \beta_0 + \beta_1 \text{Flow} + \beta_2 \Delta T_{centr} + \beta_3 \Delta T_{peri}$$

where, $\beta_0$ is the regression line intercept, and $\beta_1$, $\beta_2$, and $\beta_3$ are the weights associated with the corresponding input parameters Flow, $\Delta T_{centr}$, and $\Delta T_{peri}$.

As discussed above, to train the model, a training dataset may be used comprising historical patient data for a plurality of patients. With regards in particular to a multi-parametric linear regression model, the model is established by first constructing a model or algorithm which incorporates each of the desired input parameters as a parameter (independent variable) of the model, with a corresponding coefficient or weighting, and secondly training the constructed model based on a training dataset to thereby fit the model coefficients or weightings so as to provide a best fit between the input parameters of the training dataset and the corresponding output parameters of the training dataset. The desired input parameters form the independent variables of the model, while the target hemodynamic parameter is the dependent variable of the model. The model represents the relevant hemodynamic parameter being estimated as being a linear sum of a constant term (the intercept), and each of the dependent variables multiplied by a respective weighting or coefficient.

The training dataset will comprise training input data entries and corresponding training output data entries. The training input data entries in this case correspond to example values of the blood flow measurement for at least one arterial path, and the time difference measure, $\Delta T$, for the central and peripheral arterial paths for a given patient. The training output data entries correspond to pre-determined one or more hemodynamic parameters.

The initialized machine-learning algorithm is applied to each input data entry to generate predicted output data entries. An error between the predicted output data entries and corresponding training output data entries is used to modify the machine-learning algorithm. This process can be repeated until the error converges, and the predicted output data entries are sufficiently similar (e.g. ±1%) to the training output data entries. This is commonly known as a supervised learning technique.

For a multiparametric regression model, the training process is a process of fitting the model weightings/coefficients to the training dataset. Once the training or fitting process is complete, the model can be deployed using the weightings or coefficients obtained in the training or fitting process to map input parameters (independent variables) to the output hemodynamic parameter.

The performance or accuracy of a generated machine learning model can be assessed by running the model on a test dataset after training, and assessing the error between the output predicted values generated by the model and the actual ground truth values. For example, for a linear regression model, the performance measurements can include a goodness-of-fit of linear regression ($R^2$), a standard error (SE), the t-statistic (tStat) of the estimate, the p-value, the root mean square error (RMSE) obtained from a correlation scatter plot, and/or a coefficient of reproducibility (rpc) obtained from a Bland-Altman plot.

Although the above example transfer function uses as input parameters the blood flow measurement for the at least one arterial path, and the time difference measure, $\Delta T$, for both the central and peripheral arterial path, in further examples, the inputs to the transfer function may differ. For example, the transfer function may be adapted to accept as inputs one or more parameters derived from processing of the $\Delta T$ measures and/or the blood flow measures. Various examples were described above with reference to FIGS. 4-6 for example.

In some examples, and as explained above with reference to FIG. 4, the input parameters for the transfer function may be the PAT_cen and PAT_peri values, or a function, e.g. quotient, thereof, in combination with the blood flow measure (see explanation above for further details). In some examples, and as explained above with reference to FIG. 5, the transfer function may be adapted to accept as input parameters the PPT_cen and PPT_peri values, or a function, e.g. quotient, thereof, in combination with the blood flow measure (see explanation above for further details). In some examples, and as explained above with reference to FIG. 6, the transfer function may be adapted to accept as input parameters the $\Delta$PAT_cen and $\Delta$PAT_peri values, or a function, e.g. quotient thereof, in combination with the blood flow measure (see explanation above for further details). In some examples, the transfer function may be adapted to accept as input parameters a measure of a pulse arrival time at a defined location along each of a peripheral and arterial path, a measure of a time of heart ejection,, and the measure of blood flow.

Furthermore, it should be noted that although the above-described example of a transfer function is based on only three input parameters, in further examples, the transfer function may accept a greater number of input parameters, i.e. has a greater number of independent variables, each with a respective weighting. Additional input parameters might include for example parameters derived from the blood flow and/or $\Delta T$ measurements, and/or patient metadata such as gender and body mass index.

It is noted that although examples have been described above in which the derived hemodynamic parameter is stroke volume or cardiac output, the same inventive concept may be applied to derive any desired hemodynamic parameter. Other examples of hemodynamic parameters which could be derived include: blood velocity, stroke volume variation, systolic velocity, diastolic velocity, blood pressure.

Examples in accordance with a further aspect of the invention provide an apparatus for deriving an estimate of at least one hemodynamic parameter.

Figure 7:
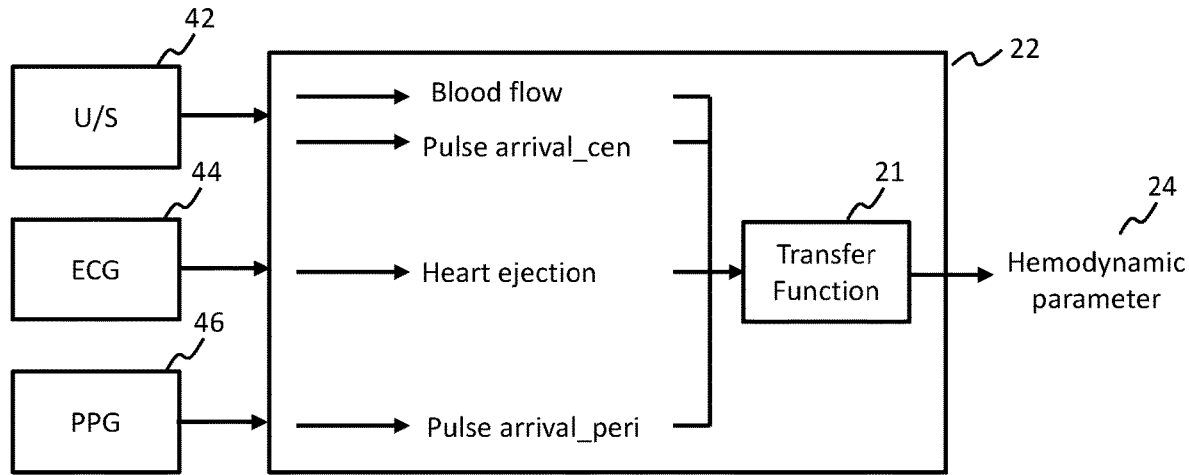
FIG. 7 schematically depicts an example apparatus according to one example embodiment.

FIG. 7 schematically outlines an example apparatus in accordance with one or more embodiments.

The apparatus comprises an ECG sensor arrangement 44 for detecting a heart ejection event.

The apparatus further comprises at least one PPG sensor 46 for optically coupling to a location along an arterial path of a subject, for detecting time of arrival of a blood pulse wave from the heart at said location.

The apparatus further comprises an ultrasound sensing means 42 for detecting blood flow through the arterial path.

The apparatus further comprises a controller 22 in accordance with any example or embodiment outlined above or described below, or in accordance with any claim of this application, operatively coupled with the ECG sensor arrangement, at least one PPG sensor and the ultrasound sensing means.

The ultrasound sensing means may comprise an ultrasound transducer arrangement. It may be configured to detect blood flow using Doppler ultrasound measurements. It may include a dedicated ultrasound processing unit for extracting from the acquired ultrasound data one or more flow measurements, and to supply these to the controller for estimating the hemodynamic parameter.

The set of measurement devices and sensors provided for this apparatus represents just one example, and further example means for acquiring the various input measurements for the controller are also possible, and have been outlined in further detail in the descriptions above.

Examples in accordance with a further aspect of the invention provide a computer-implemented method for deriving an estimate of at least one hemodynamic parameter.

Figure 8:
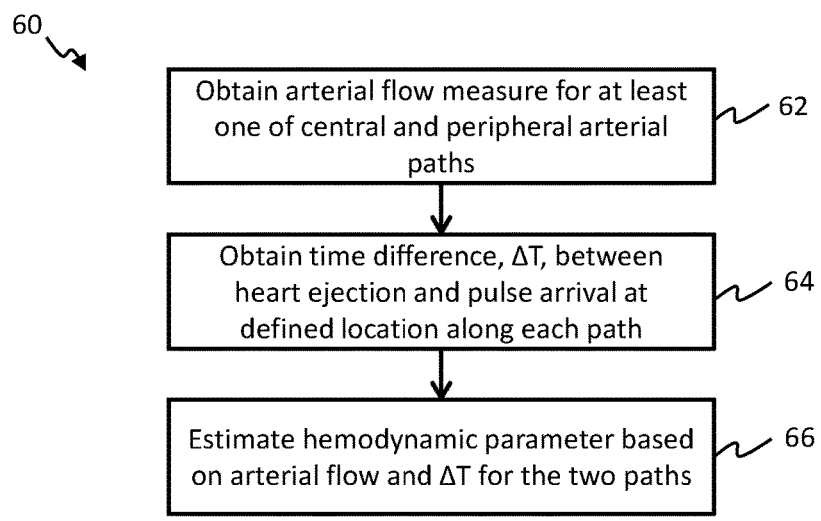
FIG. 8 outlines in block diagram form an example method according to one or more embodiments.

Steps of an example computer-implemented method 60 in accordance with one or more embodiments are outlined in block diagram form in FIG. 8.

The method 60 comprises:
receiving 62 an input indicative of an arterial flow measurement for at least one arterial path of a subject, the arterial path being a central or a peripheral arterial path;
obtaining 64 for each of a central arterial path and a peripheral arterial path a measure indicative of a time difference, $\Delta T$, between a heart ejection event and arrival of a corresponding pulse wave at a pre-determined location along the respective arterial path, as a result of blood flow from the heart to the location; and
determining 66 an estimate of the hemodynamic parameter based on a combination of: the blood flow measurement from the at least one arterial path, and the time difference measure, $\Delta T$, for each arterial path.

Implementation options and details for each of the above steps may be understood and interpreted in accordance with the explanations and descriptions provided above for the apparatus aspect of the present invention (i.e. the controller aspect).

Any of the examples, options or embodiment features or details described above in respect of the apparatus aspect of this invention (in respect of the controller) may be applied or combined or incorporated mutatis mutandis into the present method aspect of the invention.

Examples in accordance with a further aspect of the invention also provide a computer program product comprising code means configured, when run on a processor, to cause the processor to perform a method in accordance with any example or embodiment outlined above or described below, or in accordance with any claim of this application.

As discussed above, embodiments make use of a controller 22. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor or controller.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

A single processor or other unit may fulfill the functions of several items recited in the claims.

The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

If the term "adapted to" is used in the claims or description, it is noted the term "adapted to" is intended to be equivalent to the term "configured to".

Any reference signs in the claims should not be construed as limiting the scope.

The invention claimed is:

1. A system adapted to determine an estimate of at least one hemodynamic parameter of a subject, the system comprising an ECG sensor, a PPG sensor, an ultrasound device, and a controller, wherein the controller is adapted to:
receive, from the ECG sensor, a data input indicative of a heart blood ejection event;
receive, from the PPG sensor, a data input indicative of arrival of a corresponding pulse wave at a pre-determined location along a respective arterial path;
receive, from the ultrasound device, a data input indicative of an arterial blood flow measurement in at least one arterial path of the subject, the arterial path being a peripheral arterial path, or a central arterial path;
obtain for each of the peripheral arterial path and the central arterial path a measure indicative of a time difference, $\Delta T$, between the heart blood ejection event and the arrival of the corresponding pulse wave at the pre-determined location along the respective arterial path, as a result of blood flow from the heart to the location;
provide the arterial blood flow measurement for the at least one arterial path, and the measures indicative of the time difference, ΔT, for both the central and peripheral arterial path, or parameters derived therefrom, as inputs to a pre-determined transfer function, and wherein the transfer function is adapted to generate the estimate for the at least one hemodynamic parameter based on the inputs and a pre-determined functional relationship between the inputs and the at least one hemodynamic parameter; and
generate a data output indicative of the estimate of the at least one hemodynamic parameter.

2. The system as claimed in claim 1, wherein the step of obtaining the measure indicative of the time difference comprises a pulse arrival time (PAT) measurement for each of the peripheral arterial path and the central arterial path.

3. The system as claimed in claim 1, wherein the step of obtaining the measure indicative of the time difference comprises a pulse transit time (PTT) measurement for each of the peripheral arterial path and the central arterial path.

4. The system as claimed in claim 3, wherein to obtain the PTT measurement the controller is configured to obtain a pulse arrival time (PAT) measurement for each of the peripheral arterial path and the central arterial path, derive an estimate of a pre-ejection period (PEP) duration, and determine the PTT measurement for each of the peripheral arterial path and the central arterial path by subtracting the PEP duration from the PAT measurement for each of the peripheral arterial path and the central arterial path.

5. The system as claimed in claim 1, wherein the controller is configured to obtain a plurality of time difference measurements, ΔT values, for each of the peripheral arterial path and the central arterial path, corresponding to different heart cycles, and to determine a measure indicative of variation in the ΔT values over time for each arterial path, and determine the estimate of the hemodynamic parameter based on the variation in the ΔT values.

6. The system as claimed in claim 1, wherein to determine the estimate of the hemodynamic parameter the controller is configured to determine a quotient of the ΔT values for the peripheral arterial path and the central arterial path.

7. The system as claimed in claim 1, wherein the at least one hemodynamic parameter includes at least one of: cardiac output, stroke volume, or stroke volume variation.

8. The system as claimed in claim 1, wherein the controller is configured, for at least one of the peripheral arterial path and the central arterial path, to obtain both a measure of arterial flow and a measure of a time of arrival of the pulse wave at the pre-determined location along the at least one of the peripheral arterial path and the central arterial path, using a same single ultrasound sensor.

9. The system as claimed in claim 1, wherein
the heart blood ejection event is a moment of electrical activation of the heart, corresponding to the start of a pre-ejection period of the heart; or
the heart blood ejection event corresponds to a point at the end of a pre-ejection period of the heart.

10. The system as claimed in claim 1, wherein the transfer function comprises a machine learning algorithm.

11. An apparatus for deriving an estimate of at least one hemodynamic parameter, comprising:
a first sensor for detecting a heart ejection event;
a second sensor for coupling to a location along an arterial path of a subject, to detect time of arrival of a blood pulse wave from the heart at said location, the arterial path being a peripheral arterial path or a central arterial path;
a third sensor for detecting blood flow through the arterial path; and
a controller operatively coupled with the first, second and third sensor, wherein the controller is configured to:
obtain for each of a peripheral arterial path and a central arterial path a measure indicative of a time difference, ΔT, between the heart blood ejection event and the arrival of the corresponding pulse wave, as a result of blood flow from the heart to the location;
provide the arterial blood flow measurement for the at least one arterial path, and the measures indicative of the time difference, ΔT, for both the central and peripheral arterial path, or parameters derived therefrom, as inputs to a pre-determined transfer function, and wherein the transfer function is adapted to generate the estimate for the at least one hemodynamic parameter based on the inputs and a pre-determined functional relationship between the inputs and the at least one hemodynamic parameter; and
generate a data output indicative of the estimate of the at least one hemodynamic parameter.

12. The apparatus of claim 11, wherein the first sensor is an ECG sensor, the second sensor is a PPG sensor, and the third sensor is an ultrasound sensor.

13. A method for determining an estimate of at least one hemodynamic parameter, the method comprising:
receiving, from a first sensor, a data input indicative of a heart ejection event;
receiving, from a second sensor, a data input indicative of arrival of a corresponding pulse wave at a pre-determined location along a respective arterial path;
receiving, from a third sensor, for at least one arterial path of a subject a data input indicative of an arterial blood flow measurement in the arterial path, the arterial path being a peripheral arterial path, or a central arterial path;
obtaining for each of the central arterial path and the peripheral arterial path a measure indicative of a time difference, ΔT, between the heart ejection event and arrival of the corresponding pulse wave at the pre-determined location along the respective arterial path, as a result of blood flow from the heart to the location; and
providing the arterial blood flow measurement for the at least one arterial path, and the measures indicative of the time difference, ΔT, for both the central and peripheral arterial path, or parameters derived therefrom, as inputs to a pre-determined transfer function, and wherein the transfer function is adapted to generate the estimate for the at least one hemodynamic parameter based on the inputs and a pre-determined functional relationship between the inputs and the at least one hemodynamic parameter; and
generating a data output indicative of the estimate of the at least one hemodynamic parameter.

14. The computer-implemented method as claimed in claim 13, wherein the obtaining the measure indicative of the time difference for each of the peripheral arterial path and the central arterial path comprises obtaining a pulse arrival time (PAT) measurement for each arterial path, and/or a pulse transit time (PTT) measurement for each arterial path.

15. A non-transitory computer program product comprising a computer readable medium, the computer readable medium having computer readable code embodied therein, the computer readable code being configured such that, on execution by a suitable computer or processor, the computer or processor is caused to perform the method as claimed in claim 13.

\* \* \* \* \*